United States Patent [19]

Robertson

[11] Patent Number: 5,026,364
[45] Date of Patent: Jun. 25, 1991

[54] ABSORBENT ARTICLE HAVING UNITARY WAISTCAP AND WAISTBAND

[75] Inventor: Anthony J. Robertson, Blue Ash, Ohio

[73] Assignee: The Procter & Gamble Company, Cincinnati, Ohio

[21] Appl. No.: 571,000

[22] Filed: Aug. 21, 1990

Related U.S. Application Data

[63] Continuation of Ser. No. 287,944, Dec. 21, 1988, abandoned.

[51] Int. Cl.⁵ .............................................. A61F 13/15
[52] U.S. Cl. .............................. 604/385.1; 604/385.2
[58] Field of Search .................. 604/385.1, 385.2, 386

[56] References Cited

U.S. PATENT DOCUMENTS

| | | |
|---|---|---|
| 4,303,571 | 12/1981 | Jansen et al. .................. 264/299 X |
| 4,681,580 | 7/1987 | Reising et al. . |
| 4,738,677 | 4/1988 | Foreman . |
| 4,743,246 | 5/1988 | Lawson . |
| 4,753,646 | 6/1988 | Enloe . |
| 4,816,025 | 3/1989 | Foreman .................. 604/385.2 |

Primary Examiner—Richard J. Apley
Assistant Examiner—Rachel M. Healey
Attorney, Agent, or Firm—Jeffrey V. Bamber; Steven W. Miller; Richard C. Witte

[57] ABSTRACT

An integral disposable absorbent article such as a diaper is provided with an absorbent core; a liquid impervious backsheet; a liquid pervious topsheet; an elasticized waistband to enhance the fit of the diaper about the wearer; and a waistcap which presents a barrier to prevent the leakage of body exudates from the diaper. A single piece of elastomeric material serves as both the waistband and the waistcap.

22 Claims, 1 Drawing Sheet

ABSORBENT ARTICLE HAVING UNITARY WAISTCAP AND WAISTBAND

This is a continuation of U.S. application Ser. No. 07/287,944, filed on Dec. 21, 1988, now abandoned.

FIELD OF THE INVENTION

The present invention relates to absorbent articles such as disposable diapers, incontinent briefs, training pants, and the like, and more particularly, to absorbent articles having at least one unitary waistcap and waistband.

BACKGROUND OF THE INVENTION

The major function of absorbent articles such as disposable diapers and adult incontinent briefs is to absorb and contain body exudates. Such articles are thus intended to prevent body exudates from soiling, wetting, or otherwise contaminating clothing or other articles, such as bedding, that come in contact with the wearer. A common mode of failure for such products occurs when body exudates leak out of the gaps between the article and the wearer's waist to adjacent clothing because they are not immediately absorbed within the article. This is most evident with loose fecal material which is not easily absorbed by the absorbant article and tends to "float" on the liquid-receiving surface of the absorbent article.

Contemporary disposable diapers have a topsheet, a backsheet, an absorbent core, elasticized leg flaps, and an elasticized waistband to improve both wearing comfort and the ability to contain body exudates. These elasticized waistbands prove effective generally to prevent wicking and overflow from the fluid laden diaper to clothing contacting the end edges of the diaper in that the elasticized waistbands provide a gasketing action about the waist of the wearer. Despite the effectiveness of the structures, however, body exudates, especially loose fecal material, can leak through the waistband portion of the diaper and soil the wearer's clothing because the diaper does not constrain the free flow of such material nor provide a structure to hold it within the diaper so that as such material freely floats on the liquid-receiving surface of the diaper, it tends to work its way past the waistband.

Therefore, it is an object of the present invention to provide an absorbent article which has improved containment characteristics.

It is also an object of the present invention to provide an absorbent article having a waistcap wherein the distal edge is raised above the liquid-receiving surface of the absorbent article when the article is fitted on the wearer such that a channel is formed to restrain, contain and hold body exudates within the absorbent article.

It is an additional object of the present invention to provide an absorbent article having a unitary waistcap and waistband which act as a restraint against the leakage of body exudates.

These and other objects of the present invention will be more readily apparent when considered in reference to the following description and when taken in conjunction with the accompanying drawings.

SUMMARY OF THE INVENTION

In accordance with the present invention, an integral disposable absorbent article such as a diaper is provided with an elasticized waistband to enhance the fit of the diaper about the wearer's waist and a waistcap which forms a channel to prevent liquid from leaking out of the diaper. In the present invention, a single (unitary) piece of elastomeric material serves as both the waistband and the waistcap. The diaper thus generally comprises an absorbent core having a garment surface and a body surface; a liquid impervious backsheet positioned adjacent the garment surface of the absorbent core; a topsheet positioned adjacent the body surface of the absorbent core; a leg cuff disposed adjacent each longitudinal edge of the absorbent article preferably comprising a barrier cuff having a first edge and a second edge, and a spacing means operatively associated with each of said barrier cuffs for spacing the second edge of each of the barrier cuffs away from the liquid-receiving surface of the absorbent article; and a unitary waistcap/waistband disposed adjacent at least one and preferably adjacent each of the end edges of the absorbent article and comprising an outward portion that forms the waistband aspect and an inward portion having a proximal edge and a distal edge that is spaced above the liquid-receiving surface of the absorbent article so as to form the waistcap aspect.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

DETAILED DESCRIPTION OF THE INVENTION

Figure 1:
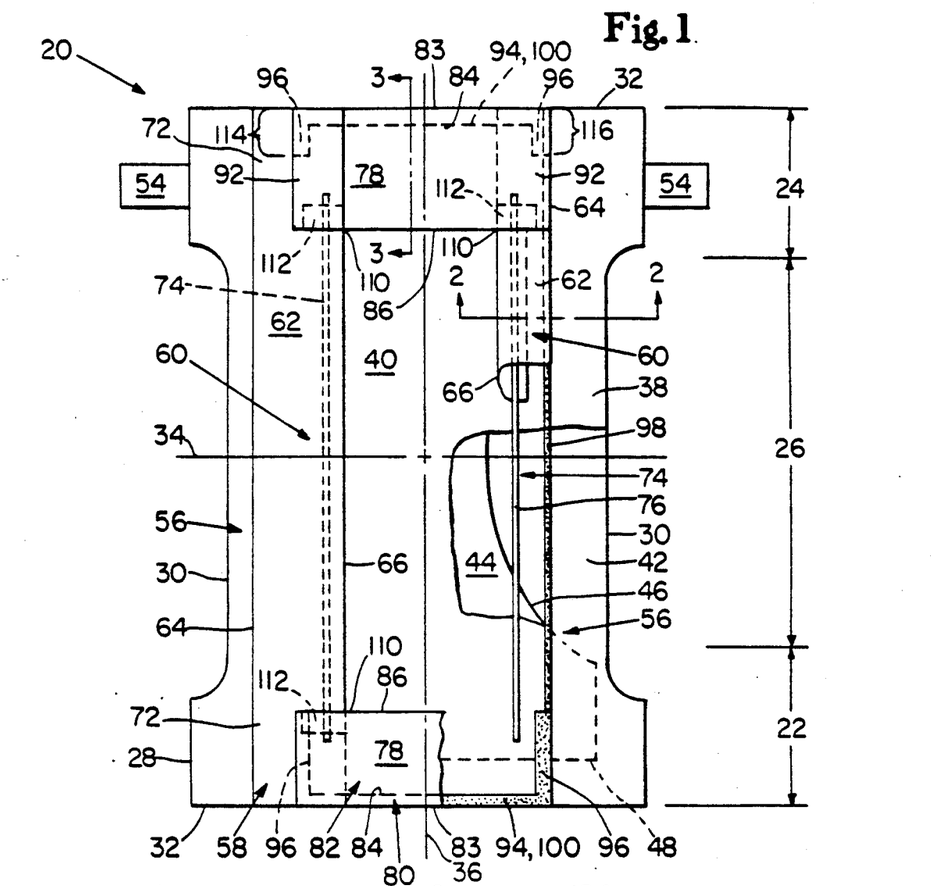
FIG. 1 is a plan view of a disposable diaper embodiment of the present invention having portions cut away to reveal underlying structure.

As used herein, the term "integral disposable absorbent article" refers to articles which absorb and contain body exudates and more specifically refers to articles which are placed against or in proximity to the body of the wearer to absorb and contain the various exudates discharged from the body, which are intended to be discarded after a single use (i.e., they are not intended to be laundered or otherwise restored or reused), and which are unitary in that they do not require separate manipulative parts like a separate holder and liner. A preferred embodiment of the integral disposable absorbent article of the present invention, diaper 20, is shown in FIG. 1. As used herein, the term "diaper" refers to a garment generally worn by infants and incontinent persons that is worn about the lower torso of the wearer. It should be understood, however, that the present invention is also applicable to other integral disposable absorbent articles such as incontinent briefs, undergarments, training pants, and the like.

FIG. 1 is a plan view of the diaper 20 of the present invention in its flat-out, uncontracted state (i.e., with all elastic induced contraction pulled out) with portions of the structure being cut-away to more clearly show the construction of the diaper 20 and with the portion of the diaper 20 which contacts the wearer facing the viewer.

The diaper 20 is shown in FIG. 1 to have a front waist region 22, a back waist region 24, a crotch region 26 and a periphery 28 which is defined by the outer edges of the diaper 20 in which the longitudinal edges 30 are designated 30 and the end edges are designated 32. The diaper 20 additionally has a lateral centerline which is designated 34 and a longitudinal centerline which is designated 36.

The diaper 20 comprises a liquid pervious topsheet 38, the liquid-receiving surface of the diaper 20 being generally defined by the topsheet 38 and being designated 40; a liquid impervious backsheet 42; an absorbent core 44 having side edges 46 and waist edges 48, a garment surface 50 and a body surface 52; a pair of tape tab fasteners 54; side flaps 56 and waist flaps 58; leg cuffs 60 each preferably comprising a barrier cuff 62 having a first edge 64, a second edge 66, an inboard surface 68, an outboard surface 70, and ends 72; spacing means 74 such as spacing elastic members 76 for spacing the second edge 66 away from the liquid-receiving surface 40; a unitary waistcap/waistband 78 having an outward portion 80 and an inward portion 82 having a proximal edge 84, a distal edge 86, an inner surface 88, an outer surface 90, and ends 92; waistband securement means 94 for securing the outward portion 80 of the unitary waistcap/waistband 78 to the diaper 20 in an elastically contractible condition adjacent the end edge 32; and a pair of closing means 96 transversely spaced from each other for securing the ends 92 of the inward portion 82 of the unitary waistcap/waistband 78 to the diaper 20 in an elastically contractible condition so that the distal edge 86 is spaced away from the liquid-receiving surface 40.

FIG. 1 shows a preferred embodiment of the diaper 20 in which the backsheet 42 has length and width dimensions generally larger than those of the absorbent core 44. The backsheet 42 extends beyond the edges of the absorbent core 44 to thereby form the periphery 28 of the diaper 20. The periphery 28 defines the outer perimeter or, in other words, the edges of the diaper 20. The periphery 28 comprises the end edges 32 and the longitudinal edges 30.

The diaper 20 has a front waist region 22 and a back waist region 24 extending, respectively, from the end edges 32 of the diaper periphery 28 toward the lateral centerline 34 of the diaper a distance of at least about 1/10, preferably from about ¼ to about ⅓ the length of the diaper 20. The waist regions comprise those portions of the diaper 20 which, when worn, encircle the waist of the wearer. The crotch region 26 is that portion of the diaper 20 between the front waist region 22 and the back waist region 24, and comprises that portion of the diaper 20 which, when worn, is positioned between the legs of the wearer and covers the lower torso of the wearer.

Figures 2, 3:
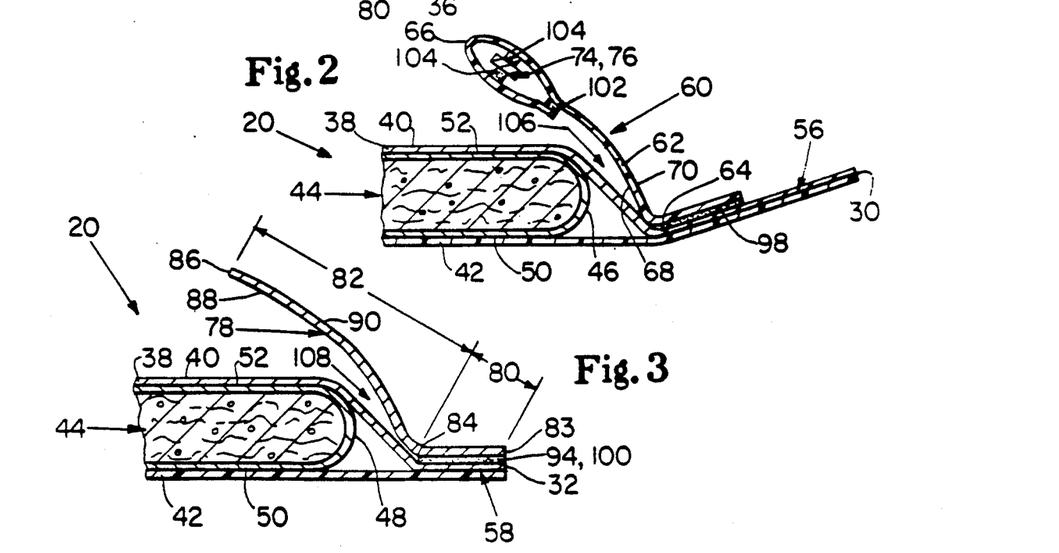
FIG. 2 is a fragmentary sectional view taken along section line 2—2 of FIG. 1.
FIG. 3 is a fragmentary sectional view taken along section line 3—3 of FIG. 1.

FIG. 2 is a fragmentary sectional view taken along line 2—2 of FIG. 1 and depicts a preferred diaper construction in the crotch region 26 of the diaper 20. The absorbent core 44 is disposed between the topsheet 38 and the backsheet 42; the topsheet 38 and the backsheet 42 extending beyond the side edge 46 of the absorbent core 44 to form the side flap 56. The leg cuff 60 preferably comprises a barrier cuff 62 and a spacing means 74 such as the spacing elastic member 76. The barrier cuff 62 is formed by affixing portions of a separate barrier cuff member to the side flap 56 adjacent the longitudinal edge 30 of the diaper 20 with edge attachment means 98 such as adhesive. The first edge 64 of the barrier cuff 62 is formed between the longitudinal edge 30 and the side edge 46 of the absorbent core 44 by joining a segment of the barrier cuff member to the topsheet 38 by the edge attachment means 98, such as an adhesive bead, so as to form a seal along the first edge 64. The second edge 66 is disposed preferably inboard of the first edge 64 and is not secured to any underlying elements of the diaper 20 in the crotch region 26. As shown in FIG. 2, the second edge 66 is formed by folding the end of the barrier cuff member back upon itself and securing it to another segment of the barrier cuff member by the attachment means 102 to form a tunnel. The spacing means 74 such as the spacing elastic member 76 is enclosed in the tunnel that is formed when the end of the barrier cuff member is folded back upon itself; the spacing elastic member 76 being secured in an elastically contractible condition in the barrier cuff 62 by the spacing elastic attachment means 104. The second edge 66 is thus spaced away from the liquid-receiving surface 40 by the elastic gathering action of the spacing elastic member 76; a channel 106 thereby being formed by at least the first edge 64, the second edge 66, and the inboard surface 68 of the barrier cuff 62. The channel 106 is shown as being open and ready to restrain, contain and hold body exudates until the diaper 20 is removed from the wearer.

FIG. 3 is a fragmentary sectional view taken along line 3—3 of FIG. 1 and depicts a preferred diaper construction in the back waist region 24 of the diaper 20. (It should be understood that the diaper construction in the front waist region 22 is similar or identical to the construction described with respect to the back waist region 24.) The absorbent core 44 is disposed between the topsheet 38 and the backsheet 42; the topsheet 38 and the backsheet 42 extending beyond the waist edge 48 of the absorbent core 44 to form the waist flap 58. The unitary waistcap/waistband 78 is formed by a single piece of elastomeric material operatively associated with the diaper 20. The outward portion 80 is operatively associated with the waist flap 58 in an elastically contractible condition adjacent the end edge 32 of the diaper 20 by the waistband securement means 94 such as an adhesive so as to form an elasticized waistband. The inward portion 82 is contiguous with the outward portion 80 and has a proximal edge 84 and a distal edge 86. The proximal edge 84 of the inward portion 82 is formed inboard of the end edge 32 of the diaper 20, preferably between the waist edge 48 of the absorbent core 44 and the outward portion 80, by joining a segment of the inward portion 82 to the waist flap 58 (the topsheet 38) by the proximal attachment means 100 such as an adhesive bead so as to form a seal along the proximal edge 84. The distal edge 86 is disposed inboard of the proximal edge 84, and in the view shown, is not secured to any underlying elements of the diaper 20, particularly the topsheet 38, so that the portion of the inward portion 82 between the closing means 96 may be spaced away from the liquid-receiving surface 40 so as to form a channel 108. Since the distal edge 86 is operatively associated with the diaper 20 in an elastically contractible condition by the pair of laterally spaced closing means 96, the distal edge 86 is shown in FIG. 3 to be spaced away from the liquid-receiving surface 40 so that the channel 108 is open and able to restrain, contain, and hold body exudates within the diaper 20.

As shown in FIG. 1, the second edge 66 of the barrier cuffs 62 and the distal edges 86 of the inward portion 82 of the unitary waistcap/waistband 78 preferably overlap at at least four points or areas which are designated corner points 110. While the edges may be disposed to overlap at only points, it is desirable that the edges overlap along a line at each intersection zone, most preferably along two lines (as is shown in FIG. 1) so that the barrier cuffs 62 and the unitary waistcap/waistband 78 overlap adjacent the corners of the diaper 20. The distal edges 86 may be secured to the second edges 66 adjacent the corner points 110 by the distal attachment means 112 so as to integrate the movement of the barrier cuffs 62 and the inward portion 82 of the unitary waistcap/waistband 78 and prevent their inversion during use. The overlapping barrier cuffs 62 and the unitary waistcap/waistband 78, thus, in this embodiment, provide a containment pocket around the periphery 28 of the diaper 20.

The topsheet 38 is positioned adjacent the body surface 52 of the absorbent core 44 and overlays a major portion of the absorbent core 44 so that exudates are discharged onto the topsheet 38 and penetrate through the topsheet 38 where they are absorbed by the absorbent core 44. The topsheet 38 extends outwardly toward the edges of the absorbent core 44 so that a major portion of the absorbent core 44 is disposed between the backsheet 42 and the topsheet 38. In the preferred embodiment shown in FIG. 1, the topsheet 38 has length and width dimensions generally larger than those of the absorbent core 44. The topsheet 38 preferably extends toward the edges of the absorbent core 44, preferably beyond the side edges 46 and the waist edges 48.

The topsheet 38 is compliant, soft feeling, and non-irritating to the wearer's skin. Further, the topsheet 38 is liquid pervious permitting liquids to readily penetrate through its thickness. A suitable topsheet 38 may be manufactured from a wide range of materials, such as porous foams, reticulated foams, apertured plastic films, natural fibers (e.g., wood or cotton fibers), synthetic fibers (e.g., polyester or polypropylene fibers) or from a combination of natural and synthetic fibers. Preferably, it is made of a hydrophobic material to isolate the wearer's skin from liquids in the absorbent core 44.

A preferred topsheet 38 comprises staple length polypropylene fibers having a denier of about 1.5, such as Hercules Type 151 polypropylene marketed by Hercules, Inc. of Wilmington, Del. As used herein, the term "staple length fibers" refers to those fibers having a length of at least about 15.9 mm (0.625 inches).

There are a number of manufacturing techniques which may be used to manufacture the topsheet 38. For example, the topsheet 38 may be woven, non-woven, spunbonded, carded, or the like. A preferred topsheet 38 is carded, and thermally bonded by means well known to those skilled in the fabrics art. Preferably, the topsheet 38 has a weight from about 18 to about 25 grams per square meter, a minimum dry tensile strength of at least about 400 grams per centimeter in the machine direction and a wet tensile strength of at least about 55 grams per centimeter in the cross machine direction.

The absorbent core 44 may be any means which is generally compressible, conformable, non-irritating to the wearer's skin, and capable of absorbing and retaining liquids and certain body exudates. A preferred absorbent core 44 has first and second opposed faces (a body surface 52 and a garment surface 50).

The absorbent core 44 may be manufactured in a wide variety of sizes and shapes (e.g., rectangular, hourglass, etc.) and from a wide variety of liquid absorbent materials commonly used in disposable diapers and other absorbent articles, such as comminuted wood pulp which is generally referred to as airfelt. Examples of other suitable absorbent materials include creped cellulose wadding, absorbent foams, absorbent sponges, super absorbent polymers, absorbent gelling materials, or any equivalent materials or combination of materials. The total absorbent capacity of the absorbent core 44 should, however, be compatible with the design exudate loading in the intended use of the diaper 20. Further, the size and absorbent capacity of the absorbent core 44 may be varied to accommodate wearers ranging from infants through adults.

The absorbent core 44 may comprise a layer of absorbent material comprising hydrophilic fibers and particles of absorbent gelling material (hydrogel) such as the absorbent structure described in U.S. Pat. No. 4,610,678 entitled "High-Density Absorbent Structure" which issued to Paul T. Wiseman and Steven A. Goldman on Sept. 9, 1986 and which patent is incorporated herein by reference. A preferred embodiment of the absorbent core 44 is a dual-layered absorbent core in a preferred configuration such as is generally described in U.S. Pat. No. 4,673,402 entitled "Absorbent Article With Dual-Layered Cores" which issued to Paul T. Wiseman, Dawn I. Houghton and Dale A. Gellert on June 16, 1987, and which is incorporated herein by reference, having an asymmetric-shaped upper layer and a lower layer. Another exemplary embodiment of an absorbent core 44 useful in the present invention is described in European Patent Application EP-A-254,476; The Procter & Gamble Company; published Jan. 27, 1988, which discloses absorbent members having a storage zone and an acquisition zone having a lower average density and a lower average basis weight per unit area than the storage zone so that the acquisition zone may effectively and efficiently rapidly acquire discharged liquid. This European patent application is hereby incorporated herein by reference.

A preferred embodiment of the diaper 20 has an hourglass-shaped absorbent core 44 and is intended to be worn by infants ranging in weight from about 5 kgs to about 12 kgs (about 12 pounds to about 26 pounds). It should be understood, however, that the size, shape, configuration, and total absorbent capacity of the absorbent core 44 may be varied to accommodate wearers ranging from infants through adults. Therefore, the dimensions, shape, and configuration of the absorbent core 44 may be varied (e.g., the absorbent core 44 may have a varying caliper, or a hydrophillic gradient, or may contain absorbent gelling materials). The absorbent core 44 is preferably a batt of airfelt about 32 cm wide (lateral dimension), about 45 cm long (longitudinal dimension) and approximately 7 cm across the narrowest part of the crotch region 26.

The backsheet 42 is positioned adjacent the garment surface 50 of the absorbent core 44 and is preferably attached thereto by attachments means (not shown) such as those well known in the art. For example, the backsheet 42 may be secured to the absorbent core 44 by a uniform continuous layer of adhesive, a patterned layer of adhesive, or an array of separate lines or spots of adhesive. Adhesives which have been found to be satisfactory are manufactured by Eastman Chemical Products Company of Kingsport, Tenn. and marketed under the tradename Eastobond A-3 and by Century Adhesives, Inc. of Columbus, Ohio and marketed under the tradename Century 5227.

The backsheet 42 is impervious to liquids and is preferably manufactured from a thin plastic film, although other flexible liquid impervious materials may also be used. The backsheet 42 prevents the exudates absorbed and contained in the absorbent core 44 from wetting articles which contact the diaper 20 such as bedsheets and undergarments. Preferably, the backsheet 42 is a polyethylene film having a thickness of from about 0.012 mm (0.5 mil) to about 0.051 cm (2.0 mils), although other flexible, liquid impervious materials may be used. As used herein, the term "flexible" refers to materials which are compliant and which will readily conform to the general shape and contours of the human body.

A suitable polyethylene film is manufactured by Monsanto Chemical Corporation and marketed in the trade as Film No. 8020. The backsheet 42 is preferably embossed and/or matte finished to provide a more clothlike appearance. Further, the backsheet 42 may permit vapors to escape from the absorbent core 44 while still preventing exudates from passing through the backsheet 42.

The size of the backsheet 42 is dictated by the size of absorbent core 44 and the exact diaper 20 design selected. In a preferred embodiment, the backsheet 42 has a modified hourglass shape extending beyond the absorbent core 44 a minimum distance of at least about 1.3 cm to about 2.5 cm (about 0.5 to about 1.0 inch) around the entire diaper 20 periphery 28.

The side flaps 56 are that portion of the diaper 20 between the periphery 28, the longitudinal edges 30, and the side edges 46 of the absorbent core 44 while the waist flaps 58 are that portion between the periphery 28, the end edges 32, and the waist edges 48 of the absorbent core 44. Thus, in a preferred embodiment of the present invention as shown in FIG. 1, the side flaps 56 are formed from the extension of the backsheet 42 and the topsheet 38 from and along the side edges 46 of the absorbent core 44 in at least the crotch region 26 and the waist flaps 58 are formed from the extension of the backsheet 42 and the topsheet 38 from and along the waist edges 48 of the absorbent core 44.

Tape tab fasteners 54 are typically applied to the back waist region 24 of the diaper 20 to provide a fastening means to hold the diaper 20 on the wearer. The tape tab fasteners 54 can be any of those well known in the art, such as the fastening tape disclosed in U.S. Pat. No. 3,848,594 entitled "Tape Fastening System For Disposable Diaper" issued to Kenneth B. Buell on Nov. 19, 1974, which is incorporated herein by reference. These tape tab fasteners 54 or other diaper 20 fastening means are typically applied near the top edge of a diaper 20 in its "in-use" configuration.

Leg cuffs 60 are disposed adjacent one or both, preferably each, of the longitudinal edges 30 of the diaper 20 to enhance the containment of exudates in the leg regions of the wearer. The leg cuffs 60 may comprise any of several means as are well known in the diaper art. An exemplary embodiment of a leg cuff construction comprises the side flap 56 and one or more elastic members as is described in detail in U.S. Pat. No. 3,860,003, entitled "Contractible Side Portions for Disposable Diaper" which issued to Kenneth B. Buell on Jan. 14, 1975, which is incorporated herein by reference. A particularly preferred leg cuff construction comprises a barrier cuff 62 and a spacing means 74 such as is described in more detail below. An alternative leg cuff construction comprises a barrier cuff 62 and spacing means 74 with a gasketing cuff to form dual cuffs such as is described in detail in U.S. Pat. No. 4,695,278, entitled "Absorbent Article Having Dual Cuffs" which issued to Michael I. Lawson on Sept. 22, 1987, which patent is incorporated herein by reference.

The leg cuffs 60 of the present invention preferably each comprise a barrier cuff 62 and a spacing means 74 to provide a barrier to restrain the free flow of body exudates along the liquid-receiving surface 40 and provide a structure to hold and contain such exudates within the diaper 20.

Each of the barrier cuffs 62 is a flexible member having a first edge 64, a second edge 66, an inboard surface 68, an outboard surface 70, and ends 72. As used herein, the term "flexible" refers to materials which are compliant and will readily conform to the general shape and contours of the body. In addition, if the spacing means 74 comprises one or more spacing elastic members 76, the barrier cuffs 62 must be contractible so that the second edges 66 may be sufficiently spaced away from the liquid-receiving surface 40 so that the channel 106 formed along the barrier cuffs 62 is open to constrain, retain and hold body exudates within the diaper 20. The barrier cuffs 62 may be manufactured from a wide variety of materials such as polypropylene, polyester, rayon, nylon, foams, plastic films, formed films, elastic films and elastic foams. A number of manufacturing techniques may be used to manufacture the barrier cuffs 62. For example, the barrier cuffs 62 may be woven, non-woven, spunbonded, carded, or the like. A particularly preferred barrier cuff 62 comprises a polypropylene material containing no finish or surfactant to render it liquid impermeable. A particularly preferred polypropylene material is manufactured by Crown Zellerbach Company as Celestra.

As shown in FIGS. 1 and 2, the barrier cuffs 62 are disposed adjacent each longitudinal edge 30 of the diaper 20. In the preferred embodiment of the present invention, the first edges 64 of the barrier cuffs 62 are joined to the diaper 20 adjacent the longitudinal edges 30, and the second edges 66 are disposed inboard of the first edges so that at least a portion of the second edges 66 are unsecured to the underlying diaper 20. The first edge 64 is preferably disposed between the longitudinal edge 30 and the longitudinal centerline 36 of the diaper 20. Most preferably, the first edge 64 is disposed between the longitudinal edge 30 and the side edge 46 of the absorbent core 44 in at least the crotch region 26 of the diaper 20.

The first edges 64 and the second edges 66 are in spaced relation to each other and define the effective width of each of the barrier cuffs 62. The first edges 64 and the second edges 66 may be in a parallel, nonparallel, rectilinear or curvilinear relationship. In addition, each of the barrier cuffs 62 may have a variety of different cross-sectional areas including circular, square, rectangular or any other shape such as that shown in FIGS. 2 and 3. Preferably, the first edges 64 are spaced from the second edges 66 in a parallel and rectilinear relationship to provide barrier cuffs 62 having uniform effective widths. Each barrier cuff 62 preferably has an effective width of at least from about 25 mm to about 50 mm, most preferably about 38 mm.

The second edges 66 are preferably disposed inboard of the first edges 64 to present a more effective barrier against the flow of exudates. The second edges 66 are maintained inboard of the first edges 64 by the closing means 96 so as to obviate their inversion. The second edges 66 may alternatively be disposed in other positions in relation to the first edges 64, such as outboard of the first edges 64.

The second edges 66 are preferably not secured to any other element of the diaper 20 in at least the crotch region 26 so that the second edges 66 may be spaced away from the liquid-receiving surface 40. The second edges 66 are preferably spaced away from the liquid-receiving surface 40 so that the barrier cuffs 62 may form a channel 106 to enhance the containment of the diaper 20. As used herein, "spaced" includes embodiments wherein the second edges 66 may assume one or more positions relative to the liquid-receiving surface 40 including at some times assuming a position adjacent the liquid-receiving surface 40.

A channel 106 is formed at least between the first edge 64 and the second edge 66 along the inboard surface 68 of each of the barrier cuffs 62. The channel 106 forms a barrier to the flow of exudates as they tend to move or float across the topsheet 38. Thus, the channel 106 restrains, contains and holds exudates within the diaper 20 until the diaper can be removed.

The barrier cuffs 62 are preferably hydrophobic and more preferably liquid impermeable so as to prevent the strikethrough of body exudates. A liquid impermeable barrier cuff 62 retards the movement of liquid through the barrier cuff 62, thereby making it more leakage resistant. The barrier cuffs 62 may be rendered liquid impermeable in any manner well known in the art such as selectively treating the barrier cuffs 62, untreating the barrier cuffs 62, by securing a separate material to the barrier cuffs 62 or by selecting a material for the barrier cuffs 62 that is inherently liquid impermeable.

The barrier cuffs 62 may additionally be provided with absorbent means secured to or within the barrier cuff 62. The absorbent means absorb and contain exudates which contact the barrier cuff 62. The absorbent means may be any means which is capable of absorbing and retaining fluids and may have any size, shape, configuration or absorbent capacity. The absorbent means may be secured to the barrier cuff 62 along the inboard surface 68 or within the barrier cuff 62. Preferably, the absorbent means is a layer of airfelt secured along the inboard surface 68 of the barrier cuff 62 and secured along the entire length and width of the inboard surface 68 of the barrier cuff 62.

A preferred embodiment of the diaper 20 shown in FIG. 1 is provided with each of the barrier cuffs 62 joined to the side flaps 56. The term "joined" includes any means for affixing the barrier cuffs 62 to the diaper 20, and includes embodiments wherein the barrier cuffs 62 are separate members directly or indirectly secured to the side flaps 56 (i.e., integral) or embodiments wherein the barrier cuffs 62 are constructed from the same member or material as an element of the diaper 20 so that the barrier cuffs 62 are a continuous and undivided element of the side flaps 56 (i.e., unitary). The barrier cuffs 62 may alternatively be joined to the backsheet 42, the absorbent core 44, the topsheet 38, or any combination of these or other elements of the diaper 20. In a preferred embodiment, the barrier cuffs 62 are integral with the side flaps 56. The integral barrier cuffs 62 are thus preferably formed by a single separate strip of material with a segment joined to the side flaps 56 by the edge attachment means 98 such as an adhesive to form the first edge 64, the second edge 66 being formed by folding an end of the material back upon itself and being secured to another segment by the attachment means 102.

The barrier cuffs 62 and the side flaps 56 are joined together in any suitable manner. As used herein, the term "joined" encompasses configurations whereby the barrier cuffs 62 are directly secured to the side flaps 56 by affixing portions of the barrier cuffs 62 directly to the topsheet 38, and configurations whereby the barrier cuffs 62 are indirectly joined to the side flaps 56 by affixing them to intermediate members which in turn are affixed to the topsheet 38. In a preferred embodiment, the barrier cuffs 62 and the side flaps 56 are joined directly to each other at the first edges 64 by the edge attachment means 98 such as adhesive or any other attachment means such as heat/pressure bonds or seals, ultrasonic bonds or any other methods as are known in the art. For example, a uniform continuous layer of adhesive, a patterned layer of adhesive, or an array of separate lines or spots of adhesive may be used. The edge attachment means 98 are preferably a hot melt adhesive such as manufactured by Eastman Chemical Products Company of Kingsport, Tenn. and marketed under the tradename Eastobond A-3 or by Century Adhesives, Inc. of Columbus, Ohio and marketed under the tradename Century 5227. (It should also be noted that the attachment means 102 herein are preferably the same type of means as the above edge attachment means 98.)

The edge attachment means 98 of the present invention for joining the first edges 64 to the side flaps 56 provide a leakage-resistant seal along the first edge 64 to present a barrier to the wicking of liquids through the topsheet 38 so as to prevent liquids from wicking underneath the barrier cuffs 62 to the edges of the diaper 20. In a preferred embodiment as shown in FIGS. 1, 2, and 3, the edge attachment means 98 are positioned along the first edges 64, preferably between the side edges 46 of the absorbent core 44 and the longitudinal edges 30 in at least the crotch region 26, such that liquids are retarded from wicking past the first edges 64 and will be contained and held within the channel 106.

The spacing means 74 for spacing the second edges 66 away from the liquid-receiving surface 40 is any member which gathers, contracts, stiffens, shortens or otherwise acts on the barrier cuffs 62 so as to cause the barrier cuff 62 to stand up to provide a channel 106 along the barrier cuff 62 that acts as a constraint against the leakage of exudates.

As shown in FIG. 1, the spacing means 74 preferably comprises a spacing elastic member 76 operatively associated with each of the barrier cuffs 62 adjacent the second edge 66. The spacing elastic member 76 is preferably secured to the barrier cuff 62 in an elastically contractible condition so that in a normally unrestrained configuration, the spacing elastic member 76 effectively contracts or gathers the second edge 66 of the barrier cuff 62. The spacing elastic member 76 can be secured to the barrier cuff 62 in an elastically contractible condition in at least two ways as is discussed in the above-referenced U.S. Pat. No. 3,860,003 which issued to Kenneth B. Buell.

The length of the spacing elastic member 76 in general is dictated by the diaper design. In the preferred embodiment illustrated in FIG. 1, the spacing elastic member 76 extends essentially the entire length of the barrier cuff 62 in the crotch region 26. In the most preferred embodiment, the spacing elastic member 76 extends longitudinally along the second edge 66 beyond the distal edges 86 of the unitary waistcap/waistband 78 (beyond the corner points 110). The spacing elastic members 77 may extend beyond the distal edges 86 any distance, including all the way to the end edges 32 of the diaper 20.

As shown in FIG. 2, the spacing elastic member 76 is operatively associated with the barrier cuff 62 by securing it within the barrier cuff 62 with a spacing elastic attachment means 104. The spacing elastic attachment means 104 should be flexible and of sufficient adhesiveness to hold the spacing elastic member 76 in its stretched condition. While the spacing elastic members 76 may be secured to the barrier cuffs 62 adjacent only the ends of the spacing elastic member 76, it is preferable to secure the entire length of the spacing elastic member 76 to the barrier cuffs 62. The spacing elastic attachment means 104 herein are preferably glue beads made of hot melt adhesive such as marketed by Findley Adhesives Incorporated, Elmgrove, Wis., as Findley Adhesives 581, although the spacing elastic members 76 may be affixed to the barrier cuffs 62 in any of several ways which are well known in the art. For example, the spacing elastic members 76 may be ultrasonically bonded or heat/pressure sealed into the barrier cuffs 62 using a variety of bonding patterns or the spacing elastic members 76 may simply be glued to the barrier cuffs 62. A more detailed description of the manner in which the spacing elastic members 76 may be positioned and secured to the barrier cuffs 62 can be found in U.S. Pat. No. 4,081,301, entitled "Method and Apparatus For Continuously Attaching Discrete, Stretched Elastic Strands to Predetermined Isolated Portions of Disposable Absorbent Products" issued to Kenneth B. Buell on Mar. 28, 1978, and in U.S. Pat. No. 4,253,461, entitled "Absorbent Brief" issued to Strickland and Visscher on Mar. 3, 1981, both of which are incorporated herein by reference. It should also be noted that one or more spacing elastic members 76 can be used to elasticize each barrier cuff 62, preferably from two to five spacing elastic members 76, most preferably three spacing elastic members 76.

A spacing elastic member 76 which has been found suitable is an elastic strand having a cross section of 0.18 mm by 1.5 mm and made from natural rubber as available from Easthampton Rubber Company of Stewart, Va., under the trademark L-1900 Rubber Compound. Other suitable spacing elastic members 76 can be made from natural rubber, such as elastic tape sold under the trademark Fulflex 9411 by Fulflex Company of Middletown, R.I. The spacing elastic member 76 may also comprise any heat shrinkable elastic material as is well known in the art. Other suitable elastic materials may comprise a wide variety of materials as are well known in the art include polyurethane films, elastomeric foams, Lycra, and formed elastic scrim.

In addition, the spacing elastic members 76 may take a multitude of configurations. For example, the width of the spacing elastic members 76 may be varied; the spacing elastic members 76 may comprise a single strand or several parallel or non-parallel strands of elastic material; or the spacing elastic members 76 may be rectilinear or curvilinear.

The spacing means 74 for spacing the distal edges 86 away from the liquid-receiving surface 40 may alternatively comprise several other elements. For example, the barrier cuffs 62 may have stiffening means disposed in or on each barrier cuff 62. The stiffening means must be sufficiently stiff so that the second edges 66 are spaced away from the liquid-receiving surface 40. Suitable materials for the stiffening means include foams, nonwoven fabrics, batting, polyethylene film, formed films, spray glues, foamed elastomerics, polyester, polyurethane, or a high loft material such as is manufactured by Carolina Formed Fabrics.

The spacing means 74 may also comprise means for shortening the length of the second edges 66 in comparison to the length of the longitudinal edges 30 of the diaper 20. The second edges 66 can be shortened by making a fold or pleat in the second edges 66. This fold or pleat is secured by any of the holding means well known to those of ordinary skill in the art, such as adhesives or heat sealing. Alternatively, a section may be cut out of the second edges 66 and the resultant edges brought together to form a butt or lapp joint. The second edges 66 may also be shortened by attaching a length of the second edge 66 to the topsheet 38 at a position different from where the second edge 66 would lie when the diaper 20 is in a flattened out condition. Other shortening techniques as are known in the art may also be used.

A waistcap and a waistband are provided at either or both of the front waist region 22 and the back waist region 24. In the description that follows, reference will be made to a waistcap and a waistband in both the front waist region 22 and the back waist region 24 of the diaper 20. While this a preferred construction, it is possible that the waistcap and the waistband are present in only one of either the front waist region 22 or the back waist region 24. When a waistcap and a waistband are present in only one waist region of the disposable diaper 20, they are preferably positioned in the front waist region 22 so as to improve the containment of urine from male wearers.

A single (unitary) piece of material serves both as the elasticized waistband and as the waistcap (barrier waist cuff). This single piece of material is herein referred to as a unitary waistcap/waistband 78. The unitary waistcap/waistband 78 thus serves two functions: it provides an elasticized waistband to enhance the fit of the diaper 20 about the waist of the wearer and to retard leakage from the waist area, and it provides a barrier waistcuff that is spaced away from the liquid-receiving surface 40 of the diaper 20 to form a channel which restrains, contains, and holds body exudates within the diaper 20 (a waistcap).

The unitary waistcap/waistband 78 is formed of an elastomeric material or materials having an elongated orientation and a relaxed orientation, and which contracts from its elongated orientation to its relaxed orientation along at least one path of response. This type of material is typically converted to the elongated orientation by tensional forces applied in any manner along at least one axis of the film or web of the material and which, when the tensional forces are removed, contracts along its path of response to its relaxed orientation, the material recovering a substantial proportion of its elongation.

Elastomeric materials useful to form the unitary waistcap/waistband 78 thus include all suitable elastic materials known in the art that are capable of forming an elastomeric material. Elastomeric materials suitable for use herein include butadiene/acrylonitrile copolymers; styrene/isoprene copolymers; polyurethane elastomers; elastomeric films such as Kraton, natural rubber, or ethylene propylene-dimonomers; elastic scrim; elastomeric foams; and heat shrinkable elastomeric materials such as ethyl vinyl acetate copolymers, polystyrene-polyolefin block copolymers, and blends thereof such as a blend of ethylene propylene rubber with ethyl vinyl acetate. A particularly preferred material for the elastomeric layer comprises an elastomeric film such as a Kraton based elastomeric film as is known in the art.

Preferably, the unitary waistcap/waistband 78 is formed from an elastomeric film laminate comprising an elastomeric film and a coverstock layer; most preferably, a laminate of a first coverstock layer, a second coverstock layer, and an elastomeric film positioned between the first coverstock layer and the second coverstock layer. The three materials are laminated together in any suitable manner as is known in the art to provide a waistcap/waistband material that is extensible in at least one direction and that is soft and pleasing to the wearer's skin.

The coverstock layers provide soft and flexible webs of material that are compliant, soft feeling, and non-irritating to the skin of the wearer so that the unitary waistcap/waistband 78 may be positioned against the skin of the wearer. Thus, the coverstock layers may be manufactured from a wide range of materials such as foams, apertured plastic films, natural fibers (e.g., wood or cotton fibers), synthetic fibers (e.g. polyester or polypropylene fibers) or from a combination of natural and synthetic fibers. There are also a number of manufacturing techniques which may be used to manufacture the coverstock layers, including, for example, that the coverstock layers may be woven or nonwoven. As used herein, the term "nonwoven" includes any material which has been formed without the use of textile weaving processes which produce a structure of individual fibers which are interwoven in an identifiable manner. Methods of making suitable nonwovens include that the material may be spunbonded, meltblown, carded, or the like. A particularly preferred coverstock layer comprises polypropylene fibers that have been spunbonded.

Examples of elastomeric laminates suitable for use as the unitary waistcap/waistband 78 are known in the art. For example, U.S. Pat. No. 4,107,363 issued to James B. Sisson on Aug. 15, 1978, discloses a cloth structure having a low modulus of elasticity in the direction or directions of stretch. This patent is incorporated herein by reference. Other suitable materials are disclosed in U.S. Pat. No. 2,957,512 issued to Wade et al. on Oct. 18, 1960; U.S. Pat. No. 4,446,189 issued to Romanek on May 1, 1984; U.S. Pat. No. 4,652,487 issued to Marman on Mar. 24, 1987; U.S. Pat. No. 4,692,368 issued to Taylor et al. on Sept. 8, 1987; and U.S. Pat. No. 4,523,407 issued to Mess on June 25, 1985.

FIGS. 1 and 3 show that each of the unitary waistcap/waistbands 78 comprises an outward portion 80 and an inward portion 82 contiguous with the outward portion 80. The inward portion 82 provides the barrier waistcuff aspect (waistcap) of the unitary waistcap/waistband 78 while the outward portion 80 provides the elasticized waistband aspect. For convenience, the two aspects will be discussed separately.

The outward portion 80 of the unitary waistcap/waistband 78 provides either a front elasticized waistband in the front waist region 22 or a rear elasticized waistband in the back waist region 24. In the embodiment illustrated in FIG. 1, the outward portion 80 of the unitary waistcap/waistband 78 extends across essentially (laterally spans) the entire lateral width of the absorbent core 44. The term "lateral width" refers to the dimension between the side edges of the absorbent core. The term "across essentially" is used in this context to indicate that the outward portion 80 need not extend absolutely across the entire width of the absorbent core 44 so long as it extends sufficiently far across the width thereof to provide the elasticized waistband function discussed herein. While this is a preferred construction, the present invention is useful in designs wherein the outward portion 80 extends across only a portion of the lateral width of the absorbent core 44, preferably at least between the second edges 66 of the barrier cuffs 62, or across a major portion of the lateral width or the entire lateral width of the diaper 20.

The extent to which the outward portion 80 extends inboard from the end edge 32 of the diaper 20, and thus the longitudinal span of the resultant waistband, can vary according to the particular construction of the diaper 20. The longitudinal span of the outward portion 80 is defined as the dimension of the outward portion 80 measured from the terminating edge 83 of the unitary waistcap/waistband 78 to the proximal edge 84 of the inward portion 82 of the unitary waistcap/waistband 78. It is preferred that the outward portion 80 have a longitudinal span less than or equal to the longitudinal span of the waist flap 58 so that the waistband aspect of the unitary waistcap/waistband 78 is positioned only in the waist flap 58. Thus, the outward portion 80 preferably has a longitudinal span of only a fraction of the total longitudinal span of the waist flap 58. The longitudinal span of the outward portion 80 is at least about 3 mm (about ⅛ inch), preferably from about 6 mm (about ¼ inch) to about 25 mm (about 1 inch), most preferably about 12 mm (about ½ inch).

The outward portion 80 is operatively associated with the diaper 20 by preferably securing it in an elastically contractible condition to the diaper 20, preferably to the waist flap 58, with at least one of the paths of response (preferably the major path of response) of the elastomeric material oriented essentially parallel to the end edge 32, so as to form a laterally extensible waistband. The outward portion 80 of the unitary waistcap/waistband 78 should be laterally extensible, that is to say, at least one of the waistbands must be relatively stable, normally gathered, at the time the diaper 20 is ready to be placed about the wearer's waist such that it is capable of elongation ("stretching") as it is fitted about the wearer's waist, and it should remain laterally extensible to form a relatively snug, but yielding fit about the wearer's waist. The outward portion 80 can be secured to the diaper 20 in an elastically contractible condition in at least two ways as is discussed in the above-referenced U.S. Pat. No. 3,860,003 which issued to Kenneth B. Buell. For example, the outward portion can be secured in an elastically contractible condition by extending the outward portion 80 to its elongated orientation, affixing the outward portion 80 to the diaper 20 while the outward portion 80 is in its elongated orientation, and allowing the outward portion 80 to assume its relaxed or contracted orientation. Alternatively, the outward portion 80 can be formed from materials which become elastic following specific treatment such as heating such that the outward portion 80 is so treated, heated, and the outward portion 80 is allowed to return to its relaxed orientation.

One or a plurality of waistband securement means 94 is positioned adjacent the end edge 32 of the diaper 20 for securing the outward portion 80 of the unitary waistcap/waistband 78 to the diaper 20 in an elastically contractible condition. Any of numerous well known means of attachment can be used to secure the outward portion 80 of the unitary waistcap/waistband 78 such as adhesive attachment means, heat/pressure bonds, ultrasonic bonds, etc.. The waistband securement means 94 preferably comprises an adhesive. Preferably, the waistband securement means 94 extends essentially across the entire outward portion 80 of the unitary waistcap/waistband 78 although other configurations would work as well.

In an alternative embodiment of the present invention, the waistband securement means 94 may comprise transverse regions of securement so as to form corrugations in the elasticized waistband to especially stiffen the waistband thereby tending to prevent waistband rollover (i.e., the bending of the waistband about itself.) An excellent discussion of how transverse regions of securement may be formed in the outward portion 80 is contained in U.S. Pat. No. 4,515,595 entitled "Disposable Diaper With Elastically Contractible Waistbands" issued to David J. Kievit and Thomas F. Osterhage on May 7, 1987, which patent is incorporated herein by reference.

The inward portion 82 of the unitary waistcap/waistband 78 provides a stand-up barrier waistcuff (waistcap) to restrain the free flow of body exudates along the liquid-receiving surface 40 and to hold and contain such exudates within the diaper 20. The inward portion 82 comprises a proximal edge 84, a distal edge 86, an inner surface 88, an outer surface 90, and ends 92. The inward portion 82 is especially effective in containing loose fecal material when positioned in the second waist region 24 and is especially effective in containing gushes of urine from male wearers when disposed in the front waist region 22.

The proximal edge 84 of each inward portion 82 is disposed adjacent the outward portion 80 of the unitary waistcap/waistband 78, and preferably between the outward portion 80 and the lateral centerline 34 of the diaper 20. Most preferably, the proximal edge 84 is disposed outboard of the waist edge 48 of the absorbent core 44 so that the proximal edge 84 is disposed between the waist edge 48 and the outward portion 80 in the waist flap 58.

The proximal edge 84 and the distal edge 86 are in spaced relation to each other and define the effective width of the inward portion 82 of the unitary waistcap/waistband 78. The proximal edge 84 and the distal edge 86 may be in a parallel, nonparallel, rectilinear or curvilinear relationship. In addition, the inward portion 82 may have a variety of different cross-sectional areas. Preferably, the proximal edges 84 are spaced from the distal edges 86 in a parallel and rectilinear relationship to provide an inward portion 82 having a uniform effective width. Each inward portion 82 preferably has an effective width of at least about 10 mm, preferably at least from about 15 mm to about 25 mm, and most preferably about 19 mm.

The distal edges 86 are preferably disposed inboard of the proximal edges 84 to present an effective barrier against the flow of exudates. The distal edges 86 are maintained inboard of the proximal edges 84 by the closing means 96 so as to obviate their inversion. While the distal edges 86 need not be maintained inboard of the proximal edges 84 such that the distal edges 86 may be disposed in other positions in relation to the proximal edges 84, such positions are not preferred.

The distal edges 86 are preferably not secured to any other element of the diaper 20 along its length between the pair of closing means 96 that secure the ends 92 of the inward portion 82 to the diaper 20 so that the distal edge 86 may be spaced away from the liquid-receiving surface 40 of the diaper 20 between the closing means 96. The distal edges 86 are spaced away from the liquid-receiving surface 40 so that the inward portion 82 may form a channel 108 to enhance the containment of the diaper 20. As used herein, "spaced" includes embodiments wherein the distal edges 86 may assume one or more positions relative to the liquid-receiving surface 40 including at some times assuming a position adjacent the liquid-receiving surface 40.

The inward portion 82 is operatively associated with the diaper 20 by being secured to the diaper 20 in an elastically contractible condition so that the inward portion 82, at least the distal edge 86, is laterally extensible and the distal edge 86 is spaced from the liquid-receiving surface 40 of the diaper 20 by the gathering of the elastomeric material. The inward portion 82 can be secured to the diaper 20 in an elastically contractible condition by extending the inward portion 82, individually or at the same time as the outward portion 80, to its elongated orientation, affixing the ends 92 of the inward portion 82 to the diaper 20 by the closing means 96 while the diaper 20 is in an uncontracted orientation, and allowing the inward portion 82 to assume its relaxed or contracted orientation. Alternatively, the inward portion 82 can be formed from materials which become elastic following specific treatment such as heating such that the inward portion 82 is so treated, heated, and the inward portion 82 is allowed to return to its relaxed orientation.

A channel 108 is formed between at least the proximal edge 84 and the distal edge 86 along the inner surface 88 of the inward portion 82. The channel 108 forms a barrier to the flow of exudates as they tend to move or float across the topsheet 38. Thus, the channel 108 restrains, contains and holds exudates within the diaper 20 until the diaper can be removed.

The inward portion 82 of the unitary waistcap/waistband 78 is preferably constructed so as to be liquid impermeable so as to prevent the strikethrough of body exudates through the inward portion 82. The inward portion 82 may be constructed to be liquid impermeable in any manner well known in the art such as by selectively treating the material, untreating the material, by securing a separate material to the inward portion 82, or by selecting a material for the inward portion 82 that is liquid impermeable. Preferably, the elastomeric film used to form the unitary waistcap/waistband 78 is already liquid impermeable such that the resultant unitary waistcap/waistband 78 is liquid impermeable.

The proximal attachment means 100 of the present invention for joining the proximal edge 84 of the inward portion 82 to the waist flap 58 provide a seal along the proximal edge 84 to present a barrier to the flow of liquids beyond the inward portion 82. The proximal attachment means 100 comprise any attachment means as are known in the art such as adhesive, heat/pressure bonds or seals, or ultrasonic bonds. The proximal attachment means 100 preferably comprise a hot melt adhesive such as manufactured by Eastman Chemical Products Company of Kingsport, Tenn. and marketed under the tradename Eastobond A-3 or by Century Adhesive, Inc. of Columbus, Ohio and marketed under the tradename Century 5227. The proximal attachment means 100 extend laterally across the entire inward portion 82 so as to form a seal line along the proximal edge 84. Thus, the proximal attachment means 100 preferably comprises a continuous line of adhesive extending laterally across the diaper 20 although the proximal attachment means 100 may alternatively comprise a patterned layer of adhesive or an array of separate lines or spots of adhesive.

As shown in FIG. 1, the proximal attachment means 100 and the waistband securement means 94 comprise the same element such that the proximal edge 84 of the inward portion 82 is immediately adjacent the outward portion 80. Such an embodiment is especially easy to manufacture since only one wide line of adhesive is required to form both the elasticized waistband and the proximal edge 84 of the waistcap. Of course, the proximal attachment means 100 may comprise a separate element from the waistband securement means 94 and be spaced inboard from the waistband securement means 94.

The closing means 96 for securing the ends 92 of the inward portion 82 of the unitary waistcap/waistband 78 in an elastically contractible condition and closed are shown in FIG. 1. The closing means 96 also provide a more comfortable fit for the wearer and obviate inversion of the distal edges 86 during application and use of the diaper 20. Inversion is generally defined as the inboard disposed distal edges 86 turning outwardly when the diaper 20 is applied to the wearer. In a preferred embodiment as shown in FIG. 1, the closing means 96 are disposed in a first closure zone 114 and a second closure zone 116. The remaining portion of the distal edge 86 is not secured to the underlying elements of the diaper 20 so that the distal edge 86 is left freely openable. In a preferred construction, the first closure zone 114 and the second closure zone 116 extend laterally across the width of the diaper less than or equal to about the lateral width of a barrier cuff 62, about 38 mm.

The closing means 96 are preferably adhesive beads consisting of hot melt adhesives such as marketed by Eastman Chemical Products Company, Kingsport, Tenn., as Eastobond A-3 or by Century Adhesives, Inc. of Columbus, Ohio as Century 5227 although other closing means 96 as are known in the art such as ultrasonic bonding or heat/pressure sealing may also be used.

The distal attachment means 112 for securing the second edges 66 and the distal edges 86 together provide a more comfortable fit for the wearer and further obviate inversion of the second edges 66 of the barrier cuffs 62 and the distal edges 86 during application and use. Inversion is generally defined as the inboard-disposed second edges 66 or distal edges 86 turning outwardly when the diaper 20 is applied to the wearer. In a preferred embodiment as shown in FIG. 1, the second edges 66 and the distal edges 86 are secured together adjacent the corner points 110. The second edges 66 and the distal edges 86 need not, however, be secured together. In a preferred embodiment as shown in FIG. 1, such distal attachment means 112 are disposed in the front waist region 22 and the back waist region 24 of the diaper 20 adjacent the corner points 110 on the barrier cuffs 62 so that the unitary waistcap/waistband 78 is positioned over or on top of the barrier cuffs 62 (i.e., the distal edges 86 are positioned over the second edges 66). In the alternative, the distal attachment means 112 may be disposed on the unitary waistcap/waistband 78 such that the barrier cuffs are positioned over the unitary waistcap/waistbands 78 (i.e., the second edges 66 are positioned over the distal edges 86).

The distal attachment means 112 are preferably adhesive beads consisting of hot melt adhesives such as marketed by Eastman Chemical Products Company, Kingsport, Tenn., as Eastobond A-3 or by Century Adhesives, Inc. of Columbus, Ohio as Century 5227 although other distal attachment means 112 as are known in the art such as ultrasonic bonding or heat/pressure sealing may also be used.

As an alternate construction, the unitary waistcap/waistband 78 can be constructed so that the inward portion 82 of the unitary waistcap/waistband 78 can be shorter in the lateral direction than the outward portion 80 or vice versa when the diaper 20 is in its in use configuration. That is to say, in the relaxed state, the unitary waistcap/waistband 78 is not a rectangle. For example, inward portion 82 is affixed to the diaper 20 by the closing means 96 as previously described. Outward portion 80 is elongated more than the distal edges 86 of the inward portion 82 and secured to the diaper 20. When the elongating forces are released, the outward portion 80 will tend to be gathered more than the inward portion 82 so that a differential elasticity is established between the two portions. This differential elasticity may also be established by choosing different elastomeric films for each portion of the unitary waistcap/waistband 78 or by deadening certain portions of the elastomeric material or by the inherent nature of the material selected for the unitary waistcap/waistband 78.

The diaper 20 is applied to a wearer by positioning the back waist region 24 under the wearer's back and drawing the remainder of the diaper 20 between the wearer's leg so that the front waist region 22 is positioned across the front of the wearer. The ends of the tape-tab fasteners 54 are then secured preferably to outwardly facing areas of the diaper 20. In this manner, the unitary waistcap/waistband 78 should be disposed to provide the dispositions and functions described hereinbefore.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An integral disposable absorbent article having longitudinal edges and end edges, the absorbent article comprising:

an absorbent core having a garment surface and a body surface;

a liquid impervious backsheet positioned adjacent said garment surface of said absorbent core;

a liquid pervious topsheet positioned adjacent said body surface of said absorbent core;

a unitary waistcap/waistband disposed to overlay the topsheet adjacent at least one of the end edges of the absorbent article, said unitary waistcap comprising a single piece of elastomeric material comprising an elastomeric film laminate comprising a coverstock layer and an elastomeric film, said unitary waistcap/waistband having an outward portion operatively associated in an elastically contractible condition with the absorbent article adjacent said end edge so as to form an elasticized waistband to enhance the fit of the absorbent article about the wearer's waist and to retard leakage from the waist area, and an inward portion contiguous with said outward portion, said inward portion having a proximal edge, a distal edge, and ends, said proximal edge being joined to the absorbent article and said distal edge spaced inboard from said proximal edge, said inward portion being operatively associated in an elastically contractible condition with the absorbent article adjacent said ends of said inward portion, at least a portion of said inward portion being unsecured to the underlying portion of the absorbent article between said ends so that said inward portion is spaced away from the liquid-receiving surface of the absorbent article to provide a stand-up waistcap to restrain the flow of body exudates along the liquid-receiving surface of said absorbent article and to contain such exudates within the absorbent article.

2. The absorbent article of claim 1 additionally comprising:

a waistband securement means for securing said outward portion of said waistcap/waistband to the absorbent article in an elastically contractible condition adjacent said end edge; and a pair of closing means transversely spaced from each other for securing said ends of said inward portion to the absorbent article in an elastically contractible condition so that said distal edge of said inward portion is gathered so as to be spaced away from the liquid-receiving surface of the absorbent article and said distal edge is maintained inboard of said proximal edge.

3. The absorbent article of claim 1 wherein said coverstock layer of said elastomeric film laminate comprises a nonwoven material.

4. The absorbent article of claim 1 additionally comprises a leg cuff positioned adjacent the longitudinal edge of the absorbent article 5. The absorbent article of claim 4 wherein said leg cuff comprises a barrier cuff disposed along each longitudinal edge of the absorbent article, each of said barrier cuffs having a first edge and a second edge, said first edge being joined to the absorbent article and said second edge disposed inboard of said first edge, wherein at least a portion of said second edge is unsecured to the underlying absorbent article, and a spacing means operatively associated with each of said barrier cuffs for spacing said second edge away from the liquid-receiving surface of the absorbent article.

6. The absorbent article of claim 1 wherein said unitary waistcap/waistband comprises a liquid impermeable material.

7. An integral disposable absorbent article having longitudinal edges and end edges, the absorbent article comprising:

an absorbent core having a garment surface, a body surface, side edges, and waist edges, wherein the dimension between said side edges is known as the lateral width of the absorbent core;

a liquid impervious backsheet positioned adjacent said garment surface of said absorbent core;

a liquid pervious topsheet positioned adjacent said body surface of said absorbent core;

a waist flap extending outwardly beyond each waist edge of said absorbent core;

a leg cuff positioned adjacent each longitudinal edge of the absorbent article;

a unitary waistcap/waistband disposed to overlay the topsheet adjacent each end edge of the absorbent article, each of said unitary waistcap/waistbands comprising a single piece of elastomeric material comprising an elastomeric film laminate comprising a coverstock layer and elastomeric film, said unitary waistcap/waistband having an outward portion operatively associated in an elastically contractible condition with the absorbent article adjacent said end edge so as to form an elasticized waistband to enhance the fit of the absorbent article about the wearer's waist and to retard leakage from the waist area, and an inward portion contiguous with said outward portion, said inward portion having a proximal edge, a distal edge, and ends, said proximal edge being joined to the absorbent article and said distal edge being spaced inboard from said proximal edge, said inward portion being operatively associated in an elastically contractible condition with the absorbent article adjacent said ends of said inward portion, at least a portion of said inward portion being unsecured to the underlying portion of the absorbent article between said ends so that said inward portion is spaced away from the liquid-receiving surface of the absorbent article to provide a stand-up waistcap to restrain the flow of body exudates along the liquid receiving surface of said absorbent article and to contain such exudates within the absorbent article;

waistband securement means for securing said outward portion of said unitary waistcap/waistband to the absorbent article in an elastically contractible condition adjacent said end edge, said waistband securement means comprising heat/pressure bonds;

a proximal attachment means for securing said proximal edge of said inward portion to the absorbent article, said proximal attachment means comprising the same element as the waistband securement means; and a pair of closing means disposed in a first closure zone and a second closure zone, said first closure zone and second closure zone extending longitudinally inboard from said proximal attachment means to said distal edge of said inward portion of the unitary waistcap/waistband, and said closing means are transversely spaced from each other for securing said ends of said inward portion to the absorbent article in an elastically contractible condition so that said distal edge of said inward portion is gathered so as to be spaced away from the liquid-receiving surface of the absorbent article and said distal edge is maintained inboard of said proximal edge.

8. The absorbent article of claim 7 wherein said outward portion extends across essentially the entire lateral width of said absorbent core.

9. The absorbent article of claim 8 wherein said outward portion is positioned only in said waist flap.

10. The absorbent article of claim 9 wherein said proximal edge of said inward portion is positioned outboard of said waist edge of said absorbent core.

11. The absorbent article of claim 10 wherein said elastomeric film laminate comprises a first coverstock layer, a second coverstock layer, and an elastomeric film positioned between said first coverstock layer and said second coverstock layer.

12. The absorbent article of claim 11 wherein said first coverstock layer and said second coverstock layer of said elastomeric film laminate each comprises a nonwoven material.

13. The absorbent article of claim 12 wherein said waistband securement means and said proximal securement means comprise a unitary securement element.

14. The absorbent article of claim 13 wherein said waistband securement means comprises an adhesive.

15. The absorbent article of claim 14 wherein said closing means comprises an adhesive.

16. The absorbent article of claim 13 wherein said waistband securement means and said closing means each comprise heat/pressure bonds.

17. The absorbent article of claim 7 where said leg cuff comprises a barrier cuff disposed along each longitudinal edge of the absorbent article, each of said barrier cuffs having a first edge and a second edge, said first edge being joined to the absorbent article and said second edge disposed inboard of said first edge, wherein at least a portion of said second edge is unsecured to the underlying absorbent article, and a spacing means for spacing said second edge away from the liquid-receiving surface of the absorbent article.

18. The absorbent article of claim 17 wherein said unitary waistcap/waistband is liquid impermeable.

19. An integral disposable absorbent article having longitudinal edges and end edges, the absorbent article comprising:
    an absorbent core having a garment surface, a body surface, side edges, and waist edges, wherein the dimension between said side edges is known as the lateral width of the absorbent core;
    a liquid impervious backsheet positioned adjacent said garment surface of said absorbent core; a liquid pervious topsheet positioned adjacent said body surface of said absorbent core;
    a waist flap extending outwardly beyond each waist edge of said absorbent core;
    a barrier cuff positioned adjacent each longitudinal edge of the absorbent article, each of said barrier cuffs having a first edge and a second edge, said first edge being joined to the absorbent article and said second edge disposed inboard of said first edge, wherein at least a portion of said second edge is unsecured to the underlying absorbent article;
    spacing means operatively associated with each of said barrier cuffs for spacing said second edge away from the liquid-receiving surface of the absorbent article;
    a unitary waistcap/waistband disposed to overlay the topsheet adjacent each end edge of the absorbent article, each of said unitary waistcap/waistbands comprising a single piece of elastomeric material consisting of an elastomeric film laminate of a first coverstock layer, a second coverstock layer, and an elastomeric film positioned between said first coverstock layer and said second coverstock layer, said unitary waistcap/waistband having an outward portion operatively associated in an elastically contractible condition with the absorbent article adjacent said end edge so as to form an elasticized waistband to enhance the fit of the absorbent article about the wearer's waist and to retard leakage from the waist area, and an inward portion contiguous with said outward portion, said inward portion having a proximal edge, a distal edge, and ends, said proximal edge being joined to the absorbent article and said distal edge, said inboard from said proximal edge, said inward portion being operatively associated in an elastically contractible condition with the absorbent article adjacent said ends of said inward portion, at least a portion of said inward portion being unsecured to the underlying portion of the absorbent article between said ends so that said inward portion is spaced away from the liquid-receiving surface of the absorbent article to provide a stand-up waistcap to restrain the flow of body exudates along the liquid-receiving surface of said absorbent article and to contain such exudates within the absorbent article, wherein said elastomeric film laminate is heat shrinkable;
    waistband securement means positioned adjacent the end edge of the absorbent article, wherein said waistband securement means are disposed in at least regions of securement which extend essentially across the entire outward portion of the waistcap/waistband for securing said outward portion of said unitary waistcap/waistband to the absorbent article in an elastically contractible condition adjacent said end edge, said waistband securement means comprising heat/pressure bonds;
    a proximal attachment means for securing said proximal edge of said inward portion to the absorbent article, said proximal attachment means comprising the same element as the waistband securement means; and
    a pair of closing means disposed in a first closure zone and a second closure zone, which first closure zone and second closure zone extend longitudinally inboard from said proximal attachment means to said distal edge of said inward portion of the unitary waistcap/waistband, and said closing means are transversely spaced from each other and secure said ends of said inward portion to the absorbent article in an elastically contractible condition so that said distal edge of said inward portion is gathered so as to be spaced away from the liquid-receiving surface of the absorbent article between said closing means and said distal edge is maintained inboard of said proximal edge, wherein said closing means also comprise heat/pressure bonds which comprise the same element as the waistband securement means and the proximal attachment means;
    wherein said second edges of said barrier cuffs and said distal edges of said inward portion overlap at at least four corner points.

20. The absorbent article of claim 19 additionally comprising a distal attachment means disposed adjacent each of said corner points for securing together said second edges and said distal edges.

21. The absorbent article of claim 20 wherein said spacing means comprises a spacing elastic member, each of said spacing elastic members extending longitudinally along said second edge beyond said distal edges.

22. The absorbent article of claim 20 wherein said distal edges of said inward portion of said unitary waistcap/waistband are disposed on top of the second edges of said barrier cuffs.

* * * * *